(12) United States Patent
Yang et al.

(10) Patent No.: US 6,423,267 B1
(45) Date of Patent: *Jul. 23, 2002

(54) STABLE OXIDIZING BROMINE FORMULATIONS, METHOD OF MANUFACTURE AND USES THEREOF FOR BIOFOULING CONTROL

(75) Inventors: Shunong Yang; William F. McCoy, both of Naperville; Anthony W. Dallmier, Aurora, all of IL (US)

(73) Assignee: Nalco Chemical Company, Naperville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/517,760

(22) Filed: Mar. 2, 2000

Related U.S. Application Data

(62) Division of application No. 09/106,602, filed on Jun. 29, 1998, now Pat. No. 6,156,229.

(51) Int. Cl.⁷ .................................. B01J 19/00
(52) U.S. Cl. .................. 422/37; 210/754; 210/758; 210/764; 252/186.1; 252/186.44; 422/28; 422/40; 422/41; 423/462
(58) Field of Search ................ 252/186.1, 186.44; 210/754, 758, 764; 423/462, 466; 422/28, 37, 40, 41

(56) References Cited

U.S. PATENT DOCUMENTS

| | | | |
|---|---|---|---|
| 3,222,276 A | | 12/1965 | Belohlav et al. |
| 3,493,654 A | | 2/1970 | Goodenough et al. |
| 3,558,503 A | | 1/1971 | Goodenough et al. |
| 4,759,852 A | | 7/1988 | Trulear |
| 4,992,209 A | | 2/1991 | Smyk et al. |
| 5,264,136 A | | 11/1993 | Howarth et al. |
| 5,589,106 A | | 12/1996 | Shim et al. |
| 5,603,840 A | | 2/1997 | Strittmatter et al. |
| 5,683,654 A | | 11/1997 | Dallmier et al. |
| 5,948,315 A | * | 9/1999 | Yang et al. .................. 252/175 |
| 6,007,726 A | * | 12/1999 | Yang et al. .................. 162/161 |
| 6,123,870 A | * | 9/2000 | Yang et al. ................ 252/186.1 |
| 6,136,205 A | * | 10/2000 | Dallmeir et al. ............ 210/754 |
| 6,156,229 A | * | 12/2000 | Yang et al. ............... 252/186.1 |
| 6,270,722 B1 | * | 8/2001 | Yang et al. .................... 162/1 |
| 6,287,473 B1 | * | 9/2001 | Yang et al. .................. 162/161 |

FOREIGN PATENT DOCUMENTS

| | | |
|---|---|---|
| EP | 0 168 253 A2 | 1/1986 |
| WO | WO96/30562 | 10/1996 |
| WO | WO97/20909 | 6/1997 |
| WO | WO97/43392 | 11/1997 |
| WO | WO99/62339 | 12/1999 |

* cited by examiner

*Primary Examiner*—Krisanne Thornton
(74) *Attorney, Agent, or Firm*—Kelly L. Cummings; Thomas M. Breininger

(57) ABSTRACT

Stable biocide formulations containing oxidizing bromine are provided for biofouling control in industrial water systems. The formulations contain at least one stable oxidizing bromine compound that is prepared from at least one oxidizing chemical reagent, at least one bromine source and at least one bromine or halogen stabilizer. The resulting products are a mixture of stable oxidizing bromine compounds that can be used as a biocide in an industrial water system.

37 Claims, No Drawings

STABLE OXIDIZING BROMINE FORMULATIONS, METHOD OF MANUFACTURE AND USES THEREOF FOR BIOFOULING CONTROL

This application is a Division of Ser. No. 09/106,602, filed Jun. 29, 1998, now U.S. Pat. No. 6,156,229.

FIELD OF THE INVENTION

The present invention relates to formulations used in biofouling control in industrial water systems. More specifically, the present invention relates to methods of preparing stable oxidizing bromine formulations and their use in biofouling control in industrial water systems.

BACKGROUND OF THE INVENTION

While elemental liquid bromine is an effective biocide, its low solubility (<4 g/100 g water), low boiling point (54.3° C.), high vapor pressure (214 mm Hg at 25° C.) and extreme corrosivity limit its use as a biocide in industrial applications. Another oxidizing bromine compound, bromate, has very little antimicrobial activity. Bromate is also very toxic to mammals and is a suspected carcinogen. Nonoxidizing inorganic bromine compounds, such as bromide, have little or no antimicrobial activity.

A mixture of an aqueous bromine solution and a bromine stabilizer has been used to generate stable oxidizing bromine compounds for use as a biocide. An unstabilized aqueous bromine solution is very acidic, unstable and emits very pungent bromine fumes. The concentration of stabilized hypobromite solution that can be made from liquid bromine, however, has been limited due to the low solubility of bromine in water.

It has also been suggested that, in addition to a bromine stabilizer, an oxidizer, such as hypochlorite, be added to activate the bromide to hypobromite. After the completion of the conversion of bromide to hypobromite, the hypobromite is stabilized by the addition of a halogen stabilizer, such as sulfamate. While this is an improved process with a higher level of oxidizing halogen content (around 14% as $Br_2$), this process still requires the separate step of synthesizing sodium hypobromite (NaOBr) as a bromine source. NaOBr is known to be very unstable and will rapidly disproportionate to bromide and bromate, both of which have little or no antimicrobial activity. In addition, because sodium hypochlorite (NaOCl) is used as an activation agent, the concentration of stabilized product is limited by the available concentration of NaOCl.

Also known are methods of generating bromine for on-site use. Such processes involve electrolytically converting bromate into active bromine compounds such as bromine, hypobromous acid, hypobromite ion and hydrogen tribromide under acidic conditions. However, because the above process generates bromine for on-site use, methods or measures for optimizing bromine stabilization are not addressed.

Therefore, methods of generating higher concentrations of stable oxidizing bromine formulations in a safer manner are needed.

SUMMARY OF THE INVENTION

The present invention satisfies the aforementioned needs by providing a method of generating a stable oxidizing bromine compound which includes the steps of mixing an alkali or alkaline earth metal bromide and an alkali or alkaline earth metal bromate in water to provide an aqueous solution, cooling the solution to a temperature of less than 25° C., preferably less than 20° C. and more preferably less than 10° C., and thereafter adding a halogen stabilizer to the solution, the halogen stabilizer being selected from the group consisting of $R-NH_2$, $R-NH-R^1$, $R-SO_2-NH_2$, $R-SO_2-NHR^1$, $R-CO-NH_2$, $R-CO-NH-R^1$ and $R-CO-NH-CO-R^1$ wherein R is a hydroxy group, an alkyl group or an aromatic group and $R^1$ is an alkyl group or an aromatic group. Preferred halogen stabilizers include urea, thiourea, creatinine, cyanuric acids, alkyl hydantoins, mono or diethanolamine, organic sulfonamides, biuret, sulfamic acid, organic sulfamates and melamine. Sulfamic acid is the most preferred halogen stabilizer.

In an embodiment, the halogen stabilizer is added to the solution in a molar amount approximately equal to the combined molar amount of alkali or alkaline earth metal bromide and alkali or alkaline earth metal bromate.

In an embodiment, the step of adding the halogen stabilizer results in the solution having a pH of less than 2.

In an embodiment, the method comprises agitating the solution for a time period of greater than 5 minutes after the step of adding the halogen stabilizer.

In an embodiment, the method comprises adjusting the solution to a pH of greater than 13 through the addition of alkali or alkaline earth metal hydroxide after the step of adding the halogen stabilizer.

In an embodiment, the step of mixing the alkali or alkaline earth metal bromide and alkali or alkaline earth metal bromate further comprises mixing the alkali or alkaline earth metal bromide and alkali or alkaline earth metal bromate in a molar ratio of alkali or alkaline earth metal bromide:bromate of about 2:1.

In an embodiment, the method of the present invention provides a stable oxidizing bromine compound which includes the steps of mixing about 2 moles of alkali or alkaline earth metal bromide and about 1 mole of alkali or alkaline earth metal bromate in water to provide an aqueous solution, followed by the step of cooling the solution to a temperature of less than 10° C., followed by the step of adding an acidic halogen stabilizer to the solution to lower the pH of the solution to less than 2, the acidic halogen stabilizer being selected from the group consisting of $R-NH_2$, $R-NH-R^1$, $R-SO_2-NH_2$, $R-SO_2-NHR^1$, $R-CO-NH_2$, $R-CO-NH-R^1$ and $R-CO-NH-CO-R^1$ wherein R is a hydroxy group, an alkyl group or an aromatic group and $R^1$ is an alkyl group or an aromatic group. Preferred halogen stabilizers include urea, thiourea, creatinine, cyanuric acids, alkyl hydantoins, mono or di ethanolamine, organic sulfonamides, biuret, sulfamic acid, organic sulfamates and melamine. The acidic halogen stabilizer is added to the solution in a molar amount approximately equal to a combined molar amount of alkali or alkaline earth metal bromide and alkali or alkaline earth metal bromate, followed by the step of agitating the solution for a time period of greater than 5 minutes, followed by the step of adding an alkali or alkaline earth metal hydroxide to the solution to increase the pH of the solution to a level greater than 13.

In an embodiment, the method of the present invention provides a method of preparing a stable oxidizing bromine compound which includes the steps of preparing a caustic solution comprising a halogen stabilizer, water and an alkali or alkaline earth metal hydroxide, adding bromine to the solution while agitating the solution and cooling the solution.

In an embodiment, the halogen stabilizer is selected from the group consisting of R—NH$_2$, R—NH—R$^1$, R—SO$_2$—NH$_2$, R—SO$_2$—NHR$^1$, R—CO—NH$_2$, R—CO—NH—R$^1$ and R—CO—NH—CO—R$^1$ wherein R is a hydroxy group, an alkyl group or an aromatic group and R$^1$ is an alkyl group or an aromatic group. Preferred halogen stabilizers include urea, thiourea, creatinine, cyanuric acids, alkyl hydantoins, mono or di ethanolamine, organic sulfonamides, biuret, sulfamic acid, organic sulfamates and melamine.

In an embodiment, the caustic solution has a pH greater than 13 after the addition of bromine.

In an embodiment, the step of adding bromine is further characterized as adding bromine in a molar amount approximately equal to the molar amount of halogen stabilizer and approximately equal to one-half of the molar amount of alkali or alkaline earth metal hydroxide.

In an embodiment, the solution is cooled to a temperature of less than 25° C.

In an embodiment, the step of adding bromine is performed without exposing the bromine to air.

In an embodiment, an alkali or alkaline earth metal hydroxide is added to the solution after the addition of bromine to increase the pH of the solution above 13.

In an embodiment, the method of the present invention provides a method of preparing a stable oxidizing bromine compound in an aqueous solution which includes the steps of dissolving an alkali or alkaline earth metal bromate salt in water to form a solution, followed by the step of adding a halogen stabilizer to the solution, the halogen stabilizer being selected from the group consisting of R—NH$_2$, R—NH—R$^1$, R—SO$_2$—NH$_2$, R—SO$_2$—NHR$^1$, R—CO—NH$_2$, R—CO—NH—R$^1$ and R—CO—NH—CO—R$^1$ wherein R is a hydroxy group, an alkyl group or an aromatic group and R$^1$ is an alkyl group or an aromatic group. Preferred halogen stabilizers include urea, thiourea, creatinine, cyanuric acids, alkyl hydantoins, mono or di ethanolamine, organic sulfonamides, biuret, sulfamic acid, organic sulfamates and melamine. Following the addition of the halogen stabilizer, bromine is added to the solution.

In an embodiment, a step of cooling the solution to a temperature of less than 25° C., preferably less than 15° C. and more preferably less than 10° C., is performed simultaneously with the step of adding the bromine to the solution.

In an embodiment, the present invention provides an aqueous biocide solution containing a stable oxidizing bromine formulation. The solution comprises at least one oxidizing bromine compound selected from the group consisting of $^-$SO$_3$NHBr and $^-$SO$_3$NBr$_2$ when sulfamate is used as the bromine stabilizer and a base in an amount sufficient to raise the pH of the solution to a level greater than 13.

In an embodiment, the base in the solution is an alkali or alkaline earth metal hydroxide.

It is therefore an advantage of the present invention to generate a stable oxidizing bromine solution using liquid bromine in a safe and efficient manner whereby no bromine fumes are generated.

It is another advantage of the present invention to generate a higher concentration of stabilized hypobromite without the need for a separate step for hypobromite generation.

Another advantage of the present invention is that it provides a method for generating water soluble solid stable oxidizing bromine compounds.

Still another advantage of the present invention is that it provides a method for generating stable oxidizing bromine compounds without unwanted by-products such as high levels of bromate.

Still another advantage of the present invention is that the method of the present invention does not generate chloride and therefore the method of the present invention provides stable oxidizing bromine formulations that are less corrosive.

Yet another advantage of the present invention is that it provides stable oxidizing bromine compounds that are safer to transport and that are non-acidic.

Yet another advantage of the present invention is that it generates stable oxidizing bromine compounds for biofouling control in industrial water systems that are more compatible with other water treatment chemicals than unstabilized oxidizing bromine compounds.

The industrial water systems include cooling water systems, cooling ponds, reservoirs, sweetwater applications, decorative fountains, pasteurizers, evaporative condensers, hydrostatic sterilizers and retorts, gas scrubber systems and air washer systems.

Another advantage of the present invention is that it provides an improved method of biofouling control in pulp and paper processing systems.

Another advantage of the present invention is that it provides an improved method of biofouling control occurring on the surfaces of equipment in contact with produced oil field waters.

Another advantage of the present invention is that it provides an improved method of biofouling control in a food processing system.

Yet another advantage of the present invention is that it provides improved biofouling control in a beverage processing system.

Still another advantage of the present invention is that it provides improved biofouling control in a recreational water system.

Another advantage of the present invention is that it provides an improved method of disinfecting a hard surface.

Another advantage of the present invention is that it provides an improved bleaching method for the laundering of soiled garments and for the manufacture of cellulosic materials.

And, another advantage of the present invention is that it provides an improved method of washing food items, such as fruit and other food items.

Other objects and advantages of the present invention will be apparent upon a review of the following detailed description and appended claims.

DETAILED DESCRIPTION OF THE INVENTION

The present invention provides a plurality of formulations and methods for generating a wide concentration of stable oxidizing bromine compounds for biofouling control in cooling water and other industrial systems.

In an embodiment, the strategy employed by the present invention utilizes a mixture of alkali or alkaline earth metal bromide and alkali or alkaline earth metal bromate in water as the bromine source. Bromate also serves as an oxidizing agent. The molar ratio of bromide to bromate is optimally 2:1. The solution is then cooled to a temperature preferably of less than 25° C. and even more preferably of less than 10° C. An acidic stabilizer or acidic stabilizing solution, such as sulfamic acid, is then added to the solution to lower the pH of the solution to less than 2. Additional stabilizer is then added to achieve equal molar amounts relative to bromine for optimal stabilization. Without being limited by theory, the following reactions are believed to occur:

$$HO-SO_2-NH_2 > H^+ + {}^-O-SO_2-NH_2 \quad (1)$$

$$2Br^- + BrO_3^- + 3H^+ > 3HBrO \quad (2)$$

$$HBrO + {}^-O-SO_2-NH_2 > {}^-O-SO_2-NH-Br, {}^-O-SO_2-NBr_2, \quad (3)$$

and other stable oxidizing bromine compounds

Since bromide, bromate and sulfamate co-exist in the resulting solution, reaction (1) to reaction (3) occurs sequentially with respect to each other. Without being limited by theory, the existence of an oxidizing bromine stabilizer and correct bromide to bromate ratio are believed to prevent the formation of bromine according to the following reaction:

$$5NaBr + NaBrO_3 + 6H^- > 3Br_2 + 6Na^- + 3H_2O \quad (4)$$

If reaction (4) were to happen instead of reaction (2), half of the raw bromine source would convert back to non-biocidal and non-oxidizing bromide according to reaction (5):

$$Br_2 + H_2O > HBrO + HBr \quad (5)$$

However, an analysis of products prepared in accordance with the present invention confirms that the reaction yield is higher than 50%. In fact, more than 80% of the bromine source was converted to oxidized bromine forms. Accordingly, the reaction yield of at least 80% was achieved.

The reaction time for reactions 1–3 at a pH of less than 2 ranges from 5 to 10 minutes with good agitation. If the product is not going to be used immediately, a strong base, such as NaOH, is added to raise the product pH to a level greater than 13 making the product thermally stable. During the pH adjustment, temperature control is important because the temperature increase by the heat generated from the acid-base reaction can cause the product to decompose. Accordingly, cooling may be necessary.

The product made with the above process has good thermostability and a high total available halogen concentration, as high as 34% as $Br_2$.

EXAMPLES

The following examples are intended to be illustrative of the present invention and to teach one of ordinary skill how to make and use the invention. These examples are not intended to limit the invention or its protection in any way.

Example I

By way of an example, synthesis of a stable oxidizing bromine product in accordance with the above-described method is carried out by mixing 21.2 grams of $NaBrO_3$, 32.8 grams of NaBr and 100 grams of water, cooling the solution to 3° C., adding 48 grams of sulfamic acid to the solution and agitating the solution for 10 minutes. Then, 48 grams of 50% aqueous NaOH is added slowly to the solution while controlling the solution temperature to a range between 4° C. and 14° C. The resulting product was a golden yellow solution with a pH of 13.77 and available halogen concentration of 25.1% as $Br_2$. In this example, the theoretical $Br_2$% is 29.9 if all of the bromine sources (bromide and bromate) were to convert to stable oxidizing bromines. Therefore, the yield is about 84%.

Example II

By way of another example, synthesis of stable oxidizing bromine formulations in accordance with the above-described method is carried out by mixing 21.2 grams of $NaBrO_3$, 32.8 grams of NaBr and 100 grams of water in a reactor, cooling the solution to 3° C., adding 44 grams of sulfamic acid to the solution and agitating the solution for 10 minutes, slowly adding 43 grams of 50% aqueous NaOH while controlling the reactor temperature between 3° C. and 14° C. The resulting product was a golden yellow solution with a pH of 14.11 and available halogen concentration of 27.7% as $Br_2$. In this example, the theoretical $Br_2$% is 31.2 if all of the bromine sources (bromide and bromate) are converted into stable oxidizing bromines. Therefore, the product yield is about 88.8%.

In another embodiment, liquid bromine is used as both oxidizer and bromine source. Sulfamate or other nitrogen base compounds are used as stabilizers. In addition, an adequate amount of alkali or alkaline earth metal hydroxide is required to maintain product pH. Formulation temperature is also extremely critical in insuring the formation of stable oxidizing bromines. Without adequate pH and temperature control, the heat generated by the exothermic reaction will cause rapid decomposition of the oxidizing species.

The process of making high concentration stable oxidizing bromine formulations consists of two steps. In the first step, a caustic stabilizing solution is prepared by mixing sulfamic acid, water and alkali or alkaline metal hydroxides (preferably NaOH, $Mg(OH)_2$ or other hydroxides). The pH of the alkali or alkaline earth metal sulfamate solution is higher than 14. Excess hydroxides are purposely added to neutralize the acids generated by the subsequent bromination step and to maintain a high pH (preferably greater than 13) in the finished product. The preferred molar ratio of sulfamate to liquid bromine is 1:1. The preferred molar ratio of hydroxide to liquid bromine is 2.2:1. The stabilizer solution can also be obtained by dissolving alkali or alkaline metal sulfamate in water and adding an appropriate amount of hydroxide.

The process is normally carried out in a jacketed glass reactor equipped with a proper mixing device. A cooling system for the reactor should be set up so that the reactor temperature can be controlled at an optimal range. An excessively high reaction temperature during the bromination step will accelerate sulfamate hydrolysis and cause decomposition of the desired product.

The second step of the process is to slowly add liquid bromine into the stabilizer solution under good agitation. Bromine is preferably added directly into the stabilizer solution through a Teflon® tube to prevent elemental bromine exposure to air. The addition rate is controlled so that the reaction temperature is preferably below 25° C. The higher the reaction temperature, the lower the product yield. If the reaction temperature gets over 35° C., sulfamate will start hydrolyzing into sulfate and ammonium. The resulting ammonium will react with and consume hypobromite and produce nitrogen gas which can be observed as vigorous foaming. With proper addition rates of liquid bromine, the liquid bromine will react instantaneously and will be stabilized. The process does not produce detectable bromine fumes.

The product made with the above-described process was found to include no detectable bromate (less than 50 ppm with ion chromatography analysis); no detectable product concentration change was observed during a 2 month storage period at room temperature. For a 16.2% (as $Br_2$) product, the product has a half life of 74.5 days at 57° C.

Example III

By way of an example, synthesis of a stable oxidizing bromine product using the above-described method is achieved by mixing 52.16 grams of sulfamic acid, 42.0 grams of water and 128.0 grams of 50% aqueous NaOH in a 500 ml three-neck glass reactor. The mixture is cooled to a temperature of about 3° C. under constant agitation and refrigerated in a water bath. 82.5 grams of liquid bromine (99.8% $Br_2$) is slowly added to the solution and the reaction temperature is controlled and maintained below 10° C. The resulting solution has a pH of 12.5. The solution pH was increased to a level greater than 13 by adding 3.0 grams of 50% NaOH. The bromine content in the resulting solution was 26.2% as $Br_2$ while a theoretical content if 100% conversion is achieved is 27.0% as $Br_2$.

After overnight storage at room temperature (21° C.), the formation of large amounts of crystals was observed in the solution. Using a 0.45 μm filter to separate the crystal from the liquid, followed by dehydration of the crystals under vacuum overnight, 46.8% as $Br_2$ was detected in the solid product while 18.7% of bromine content as $Br_2$ remained in the liquid. The solid product was found to be extremely water soluble. Accordingly, the present invention provides a solid stable oxidizing bromine product which is water soluble.

The solid product obtained in the above example has a very high concentration of stable oxidizing bromine compounds. The remaining content is believed to be water, excess NaOH and NaBr.

Other hybrid methods can be used to generate stable oxidizing bromine compounds. One such method consists of using bromate salt as an oxidizer and bromine source, liquid bromine as an oxidizer, bromine source and acidic compound and sulfamate or another suitable halogen stabilizer as the bromine stabilizer. The reaction mechanism would be as follows:

$Br_2 + H_2O > 2H^+ + Br^- + OBr^-$ (6)

$BrO_3^- + 2Br^- + H^+ > 3OBr^-$ (7)

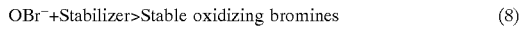
$OBr^- + Stabilizer > Stable\ oxidizing\ bromines$ (8)

The process can be carried out by dissolving bromate salt and water, adding sulfamate or other stabilizer to the solution, slowly adding liquid bromine, adjusting the pH to a level greater than 13 by adding NaOH, if the resulting product is to be stored for a long period of time. The process should be conducted at a temperature less than 25° C., especially during the addition of liquid bromine.

In an embodiment, the stable oxidizing bromine compound of the present invention can be used to provide improved biofouling control in industrial water systems, pulp and paper processing systems, food and beverage processing systems and recreational water systems. The stable oxidizing bromine compound of the present invention can also be used as a bleaching agent and to disinfect a hard surface. By way of example only, the present invention may be added to an aqueous media used to transport food through various processing systems and also to disinfect process equipment and waste water streams.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. A stable oxidizing bromine compound prepared by the following steps:

mixing an alkali or alkaline earth metal bromide and an alkali or alkaline earth metal bromate in water to provide an aqueous solution, cooling the solution to a temperature less than 25° C., and adding a halogen stabilizer to the solution, the halogen stabilizer being selected from the group consisting of $R-NH_2$, $R-NH-R^1$, $R-SO_2-NH_2$, $R-SO_2-NHR^1$, $R-CO-NH_2$, $R-CO-NH-R^1$ and $R-CO-NH-CO-R^1$ wherein R is a hydroxy group, an alkyl group or an aromatic group and $R^1$ is an alkyl group or an aromatic group.

2. The stable oxidizing bromine compound of claim 1 wherein the halogen stabilizer is selected from the group consisting of urea, thiourea, creatinine, cyanuric acids, alkyl hydantoins, monoethanolamine, diethanolamine, organic sulfonamides, biuret, sulfamic acid, organic sulfamates and melamine.

3. In a method for the control of biofouling in an industrial water system in which an oxidizing agent is added to control the biofouling, the method comprising using as the oxidizing agent the stable oxidizing bromine compound of claim 1.

4. In a method for the control of biofouling in a pulp and paper processing system in which an oxidizing agent is added to control the biofouling, the method comprising using as the oxidizing agent the stable oxidizing bromine compound of claim 1.

5. In a method for the control of biofouling occurring on the surfaces of equipment in contact with produced oil field waters in which an oxidizing agent is added to control the biofouling, the method comprising using as the oxidizing agent the stable oxidizing bromine compound of claim 1.

6. In a method for the control of biofouling in a food processing system in which an oxidizing agent is added to control the biofouling, the method comprising using as the oxidizing agent the stable oxidizing bromine compound of claim 1.

7. In a method for the control of biofouling in a beverage processing system in which an oxidizing agent is added to control the biofouling, the method comprising using as the oxidizing agent the stable oxidizing bromine compound of claim 1.

8. In a method for the control of biofouling in a recreational water system in which an oxidizing agent is added to control the biofouling, the method comprising using as the oxidizing agent the stable oxidizing bromine compound of claim 1.

9. In a method of disinfecting a hard surface in which an oxidizing agent is added to disinfect the hard surface, the method comprising using as the oxidizing agent the stable oxidizing bromine compound of claim 1.

10. In a method of washing food items in which an oxidizing agent is added to disinfect the food items, the method comprising using as the oxidizing agent the stable oxidizing bromine compound of claim 1.

11. In a method of laundering soiled garments and manufacturing cellulosic materials in which an oxidizing agent is used as a bleaching agent, the method comprising using as the oxidizing agent the stable oxidizing bromine compound of claim 1.

12. A stable oxidizing bromine compound prepared by the following steps:

mixing about 2 moles of alkali or alkaline earth metal bromide and about 1 mole of alkali or alkaline earth metal bromate in water to provide an aqueous solution, cooling the solution to a temperature of less than 10° C., adding an acidic halogen stabilizer to the solution to lower the pH of the solution to less than 2, the acidic halogen stabilizer being selected from the group consisting of urea, thiourea, creatinine, cyanuric acids, alkyl hydantoins, monoethanolamine, diethanolamine, organic sulfonamides, biuret, sulfamic acid, organic sulfamates and melamine, the acidic halogen stabilizer being added in a molar amount approximately equal to a combined molar amount of alkali or alkaline earth metal bromide and alkali or alkaline earth metal bromate, agitating the solution for a time period greater than 5 minutes, and adding an alkali or alkaline earth metal hydroxide to the solution to increase the pH of the solution to greater than 13.

13. In a method for the control of biofouling in an industrial water system in which an oxidizing agent is added to control the biofouling, the method comprising using as the oxidizing agent the stable oxidizing bromine compound of claim 12.

14. A stable oxidizing bromine compound prepared by the following steps:

preparing a caustic solution comprising a halogen stabilizer, water and an alkali or alkaline earth metal hydroxide, the halogen stabilizer being selected from the group consisting of R—$NH_2$, R—NH—$R^1$, R—$SO_2$—$NH_2$, R—$SO_2$—$NHR^1$, R—CO—$NH_2$, R—CO—NH—$R^1$ and R—CO—NH—CO—$R^1$ wherein R is a hydroxy group, an alkyl group or an aromatic group an $R^1$ is an alkyl group or an aromatic group, adding bromine to the solution while mixing the solution, and cooling the solution.

15. The stable oxidizing bromine compound of claim 14 wherein the halogen stabilizer is selected from the group consisting of urea, thiourea, creatinine, cyanuric acids, alkyl hydantoins, monoethanolamine, diethanolamine, organic sulfonamides, biuret, sulfamic acid, organic sulfamates and melamine.

16. In a method for the control of biofouling in an industrial water system in which an oxidizing agent is added to control the biofouling, the method comprising using as the oxidizing agent the stable oxidizing bromine compound of claim 14.

17. In a method for the control of biofouling in a pulp and paper processing system in which an oxidizing agent is added to control the biofouling, the method comprising using as the oxidizing agent the stable oxidizing bromine compound of claim 14.

18. In a method for the control of biofouling occurring on the surfaces of equipment in contact with produced oil field waters in which an oxidizing agent is added to control the biofouling, the method comprising using as the oxidizing agent the stable oxidizing bromine compound of claim 14.

19. In a method for the control of biofouling in a food processing system in which an oxidizing agent is added to control the biofouling, the method comprising using as the oxidizing agent the stable oxidizing bromine compound of claim 14.

20. In a method for the control of biofouling in a beverage processing system in which an oxidizing agent is added to control the biofouling, the method comprising using as the oxidizing agent the stable oxidizing bromine compound of claim 14.

21. In a method for the control of biofouling in a recreational water system in which an oxidizing agent is added to control the biofouling, the method comprising using as the oxidizing agent the stable oxidizing bromine compound of claim 14.

22. In a method of disinfecting a hard surface in which an oxidizing agent is added to disinfect the hard surface, the method comprising using as the oxidizing agent the stable oxidizing bromine compound of claim 14.

23. In a method of washing food items in which an oxidizing agent is added to disinfect the food items, the method comprising using as the oxidizing agent the stable oxidizing bromine compound of claim 14.

24. In a method of laundering soiled garments and manufacturing cellulosic materials in which an oxidizing agent is used as a bleaching agent, the method comprising using as the oxidizing agent the stable oxidizing bromine compound of claim 14.

25. A stable oxidizing bromine compound prepared by the following steps:

preparing a caustic solution comprising a halogen stabilizer, water and an alkali or alkaline earth metal hydroxide, the halogen stabilizer being selected from the group consisting of urea, thiourea, creatinine, cyanuric acids, alkyl hydantoins, monoethanolamine, diethanolamine, organic sulfonamides, biuret, sulfamic acid, organic sulfamates and melamine, adding bromine to the solution in a molar amount approximately equal to a molar amount of halogen stabilizer and approximately one-half of a molar amount of alkali or alkaline earth metal hydroxide and without exposing the bromine to air, mixing the solution, the solution having a pH after the mixing step of greater than 13, cooling the solution to a temperature of less than 25° C., and adding an alkali or alkaline earth metal hydroxide to the solution to increase the pH of the solution above 13.

26. In a method for the control of biofouling in an industrial water system in which an oxidizing agent is added to control the biofouling, the method comprising using as the oxidizing agent the stable oxidizing bromine compound of claim 25.

27. A stable oxidizing bromine compound prepared by the following steps:

dissolving an alkali or alkaline earth metal bromate salt in water to form a solution, adding a halogen stabilizer to the solution, the halogen stabilizer being selected from the group consisting of R—$NH_2$, R—NH—$R^1$, R—$SO_2$, —$NH_2$, R—$SO_2$—$NHR^1$, R—CO—$NH_2$, R—CO—NH—$R^1$ and R—CO—NH—CO—$R^1$ wherein R is a hydroxy group, an alkyl group or an aromatic group and $R^1$ is an alkyl group or an aromatic group, and adding bromine to the solution.

28. The stable oxidizing bromine compound of claim 27 wherein the halogen stabilizer is selected from the group consisting of urea, thiourea, creatinine, cyanuric acids, alkyl hydantoins, monoethanolamine, diethanolamine, organic sulfonamides, biuret, sulfamic acid, organic sulfamates and melamine.

29. In a method for the control of biofouling in an industrial water system in which an oxidizing agent is added to control the biofouling, the method comprising using as the oxidizing agent the stable oxidizing bromine compound of claim 27.

30. In a method for the control of biofouling in a pulp and paper processing system in which an oxidizing agent is added to control the biofouling, the method comprising using as the oxidizing agent the stable oxidizing bromine compound of claim 27.

31. In a method for the control of biofouling occurring on the surfaces of equipment in contact with produced oil field waters in which an oxidizing agent is added to control the biofouling, the method comprising using as the oxidizing agent the stable oxidizing bromine compound of claim 27.

32. In a method for the control of biofouling in a food processing system in which an oxidizing agent is added to control the biofouling, the method comprising using as the oxidizing agent the stable oxidizing bromine compound of claim 27.

33. In a method for the control of biofouling in a beverage processing system in which an oxidizing agent is added to control the biofouling, the method comprising using as the oxidizing agent the stable oxidizing bromine compound of claim 27.

34. In a method for the control of biofouling in a recreational water system in which an oxidizing agent is added to control the biofouling, the method comprising using as the oxidizing agent the stable oxidizing bromine compound of claim 27.

35. In a method of disinfecting a hard surface in which an oxidizing agent is added to disinfect the hard surface, the method comprising using as the oxidizing agent the stable oxidizing bromine compound of claim 27.

36. In a method of washing food items in which an oxidizing agent is added to disinfect the food items, the method comprising using as the oxidizing agent the stable oxidizing bromine compound of claim 27.

37. In a method of laundering soiled garments and manufacturing cellulosic materials in which an oxidizing agent is used as a bleaching agent, the method comprising using as the oxidizing agent the stable oxidizing bromine compound of claim 27.

* * * * *